US009008372B2

(12) United States Patent
Shako et al.

(10) Patent No.: US 9,008,372 B2
(45) Date of Patent: *Apr. 14, 2015

(54) METHOD FOR DETERMINATION OF SPATIAL DISTRIBUTION AND CONCENTRATION OF CONTRAST COMPONENTS IN A POROUS AND/OR HETEROGENEOUS SAMPLE

(75) Inventors: Valery Vasilievich Shako, Domodedovo (RU); Nikita Ilyich Ryzhikov, Moscow (RU); Dmitry Nikolaevich Mikhailov, Moscow (RU)

(73) Assignee: Schlumberger Technology Corporation, Sugar Land, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/119,661

(22) PCT Filed: May 31, 2011

(86) PCT No.: PCT/RU2011/000378
§ 371 (c)(1),
(2), (4) Date: Feb. 19, 2014

(87) PCT Pub. No.: WO2012/165991
PCT Pub. Date: Dec. 6, 2012

(65) Prior Publication Data
US 2014/0192953 A1  Jul. 10, 2014

(51) Int. Cl.
*G06K 9/00* (2006.01)
*G01N 23/04* (2006.01)
(52) U.S. Cl.
CPC ........ *G01N 23/046* (2013.01); *G01N 2223/616* (2013.01); *G01N 2223/646* (2013.01); *G01N 2223/649* (2013.01); *G01N 2223/419* (2013.01)

(58) Field of Classification Search
CPC ................ G01N 23/046; G01N 2223/419
USPC ........... 378/45, 48, 49, 50, 51, 53, 55, 56, 57, 378/62; 382/128–131, 168, 170–172
See application file for complete search history.

(56) References Cited

U.S. PATENT DOCUMENTS

| 4,991,092 | A | * | 2/1991 | Greensite | 382/131 |
| 5,027,379 | A | * | 6/1991 | Hunt et al. | 378/4 |
| 5,469,488 | A | | 11/1995 | Ono | |
| 6,738,144 | B1 | | 5/2004 | Dogariu | |
| 7,319,739 | B2 | | 1/2008 | Heismann | |
| 2003/0068074 | A1 | * | 4/2003 | Hahn | 382/128 |
| 2004/0258305 | A1 | * | 12/2004 | Burnham et al. | 382/171 |
| 2005/0010106 | A1 | | 1/2005 | Lang et al. | |

OTHER PUBLICATIONS

International Search Report of PCT Application No. PCT/RU2011/000378 dated Mar. 1, 2012: p. 1.
Gonzalez et al., "Chapter 10: Image Segmentation," Digital Image Processing, Second Edition, Prentice Hall: New Jersey, 2002: pp. 602.606.
Gupta et al., "A Gaussian-Mixture-Based Image Segmentation Algorithm," Pattern Recognition, 1998, vol. 31(3): pp. 315-325.

* cited by examiner

*Primary Examiner* — Samir Ahmed

(57) ABSTRACT

A method for determination of a spatial distribution and concentration of contrast components in a porous sample comprises the steps of scanning a sample with X-ray and obtaining a computer tomographic image of the sample. Then an area of interest inside the obtained computer tomographic image is selected and a first cross-section of the computer tomographic image is defined. Spatial distribution and concentration of contrast components inside the area of interest are determined by analyzing histograms of grayness distribution in the cross-sections of the computer tomographic image starting with the reference cross-section.

4 Claims, 4 Drawing Sheets

| | |
|---|---|
| Count: 5615852 | Min: 5842 |
| Mean: 10879.524 | Max: 55880 |
| StdDev: 1612.837 | Mode: 11998 (420583) |
| Bins: 256 | Bin Width: 195.461 |

7736                                           15033

Count: 23293      Min: 7736
Mean: 11838.955    Max: 15033
StdDev: 492.525     Mode: 11847 (617)
Bins: 256             Bin Width: 28.504

METHOD FOR DETERMINATION OF SPATIAL DISTRIBUTION AND CONCENTRATION OF CONTRAST COMPONENTS IN A POROUS AND/OR HETEROGENEOUS SAMPLE

CROSS-REFERENCE TO RELATED APPLICATION

This application is a U. S. National Stage Application under 35 U.S.C. §371 and claims priority to Patent Cooperation Treaty Application No. PCT/RU2011/000378 filed May 31, 2011, which is incorporated herein by reference in its entirety.

FIELD OF THE INVENTION

The present invention relates generally to the methods for determination of spatial distribution and concentration of contrast components (mineral grains, components inside pore space, inclusions) in materials by analysing X-ray tomography data and can be used, for example, for calculation of fraction of contrast minerals in rock sample, diagnostic of tumor (cancerous or innocent) sizes in medicine (after using of special contrast agents), crack detection of composite and geo-materials.

BACKGROUND OF THE INVENTION

Powerful nondestructive method for analysis of contrast components in heterogeneous or porous medium is X-ray micro Computed Tomography (XmCT). This technique provides 3D object structure composed of cross-section images of the internal structure with acquisition of grayscale which represents the X-ray absorption distribution (attenuation coefficients) within the object. The idea of correlation between the gray values distribution in X-ray CT image and material densities distribution is described in US Pat. No. 2005/0010106).

Computer tomography technique is based on the interaction of X-rays with material. Passing through an object X-rays will be attenuated depending on the physical density and atomic number of the studied object and on the used X-ray energies. This attenuation information is collected on 2D XmCT image.

Depending on X-ray attenuation coefficient, each point of the black-white slice of object is characterized by different grayness. Because attenuation coefficient depends on material, through X-ray has passed, different materials are characterized by different grayness that allow us to separate individual materials and estimate it's fraction on each X-ray section.

Most widespread method of image recognizing is thresholding. Thresholding is method to separate object of interest from "background" (i.e. other objects) which is based on choosing of optimal threshold level of grayness. All points ("pixels") of the black-white X-ray image of object which grayness is lower then the threshold value are supposed to belong to object (or background, depending what is more bright).

Special type of this method is histogram based thresholding which is developed for case when an image have only two principal ("dark" and "light") grayscale regions (see, for example, Gupta L., Sortrakul T. A Gaussian-mixture based image segmentation algorithm. Pattern Recognition, Vol. 31, No. 3, p. 315-325,1998).

Principle disadvantage of thresholding technique is sensitivity of results to selected value of threshold and thus requires a priori information about analyzed parametres.

This invention describes new method which is based on solving of inverse problem while analysis of histogram and provide deterministic solution.

SUMMARY OF THE INVENTION

A method for determination of spatial distribution and concentration of contrast components in a porous sample comprises the steps of scanning a sample with X-ray and obtaining a computer tomographic image of the sample. Then an area of interest inside the obtained computer tomographic image is selected and a first cross-section of the computer tomographic image (let us call it as reference cross-section and assign a number k=1) is defined. Histograms of grayness distribution in the cross-sections of the computer tomographic image are obtained. Spatial distribution and concentration of contrast components inside the area of interest are determined by analyzing histograms of grayness distribution in the cross-sections of the computer tomographic image, starting with the reference cross-section.

According to the first embodiment of the invention number of the components is defined as the number of peaks on the histogram of grayness distribution inside the area of interest on the reference cross-section. The histogram $I_i^1(z)$ of grayness distribution for each component inside the reference cross-section (k=1) is approximated by normal distribution (Gaussian function):

$$I_i^1(z) = A_i^1 \exp\left[-\left(\frac{z - B_i^1}{C_i^1}\right)^2\right]$$

wherein i is index of a component; I is "intensity" (total number of pixels) of grayness z; $A_i^1$, $B_i^1$, $C_i^1$ are adjustable parameters; upper index "1" corresponds to number of cross-section (k=1). Adjustable parameters for all components are crudely estimated from the histogram of grayness distribution inside the area of interest. Accurate estimation of adjustable parameters for the components is made by minimization of module of difference between the histogram of grayness distribution inside the area of interest of the reference cross-section and sum of normal distributions corresponding to individual components $$\sum_{j=1}^{M}\left[H^1(z_j) - \sum_{i=1}^{N} A_i^1 \exp\left(-\left(\frac{z_j - B_i^1}{C_i^1}\right)^2\right)\right] \to 0 \quad (1)$$

wherein j is index of grayscale; M is total number of grayscales; N is total number of different components.

The fraction $a_i^1$ of the individual components inside the reference cross-section inside of the computer tomographic image is calculated as:

$$a_i^1 = \int A_i^1 \exp\left[-\left(\frac{z - B_i^1}{C_i^1}\right)^2\right] dz \quad (2)$$

Obtained parameters of Gaussians $A_i^1$, $B_i^1$, $C_i^1$ of the reference cross-section are used as initial parameters for minimization of module of difference between the real histogram of grayness distribution and it's approximation by sum of normal distributions (1) for next cross-section of X-ray image (k=2) and so an.

To reconstruct the distribution and concentration of the contrast components along the sample, the mininization of module of difference between the real histogram of grayness distribution and it's approximation by sum of normal distributions (1) and the expression (2) are applied to all cross-sections inside area of interest of the computer tomographic image (k=1... K).

According to the second embodiment of the invention the sub-areas each containing only one individual component are selected inside the area of interest on the reference cross-section and histograms of grayness distribution of the individual components are obtained. All histograms are normalized by their area, i.e. by number of pixels. The histograms of all individual components are transformed to general scale. Histogram of the area of interest of the reference cross-section is approximated by sum of histograms of individual components with some weight coefficients, corresponding to the areas that individual components occupy on this cross-section of the computer tomographic image.

Weight coefficients are obtained by minimization of module of difference between the real histogram of the area of interest of the reference cross-section (k=1) and sum of histograms of individual components:

$$\left[\sum_{j=1}^{M}(|A_j^1 - b^1 B_j^1 c^1 C_j^1 - \ldots|)\right] \to 0 \quad (3)$$

wherein $A_j^1$, $B_j^1$, $C_j^1$, ... are vectors of values of histograms, $b^1$, $c^1$ etc are weight coefficients; j is index of grayscale; M is total number of grayscales; upper index "1" corresponds to number of cross-section (k=1).

Weight coefficients $b^1$, $c^1$ etc correspond to areas that individual components occupied on the reference cross-section of the histograms of grayness distribution in the cross-sections of the computer tomographic image.

To reconstruct distribution and concentration of the contrast components along the sample, the procedure described above and including the mininization (3), is applied to all cross-sections inside the area of interest of the computer tomographic image (k=1... K).

In the case of bad convergence of this problem, it is possible to extend the sub-areas containing individual components.

DETAILED DESCRIPTION OF THE INVENTION

According to the first embodiment of the invention a porous sample (artificial sample, consisting of sand grains and liquid glass as cement material) is scanned with X-ray and a computer tomographic image of the sample is obtained. Then an area of interest inside of this computer tomographic image is selected and a first cross-section of the computer tomographic image (let us call it as reference cross-section and assign a number k=1) is defined. Under an area of interest we understand a sub-area of 3D X-ray computer tomographic image which is selected for detailed analysis. This area can be selected because it includes some specific features (microfractures, defect or specific inclusion) or as typical volume of image to reduce simulation time (if initial 3D X-ray image is too large for analysis).

Figure 1:
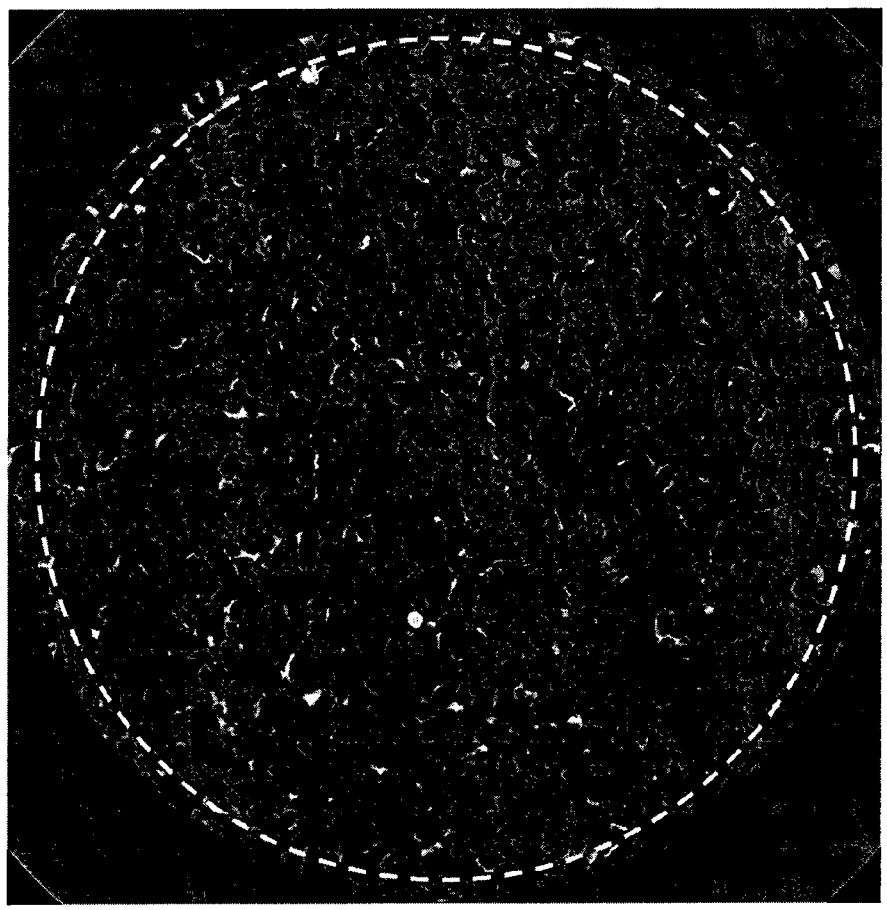
FIG. 1 shows an example of selecting an area of interest on the cross-section of the computer tomographic image and obtaining the histogram of grayness distribution.
Figure 1:
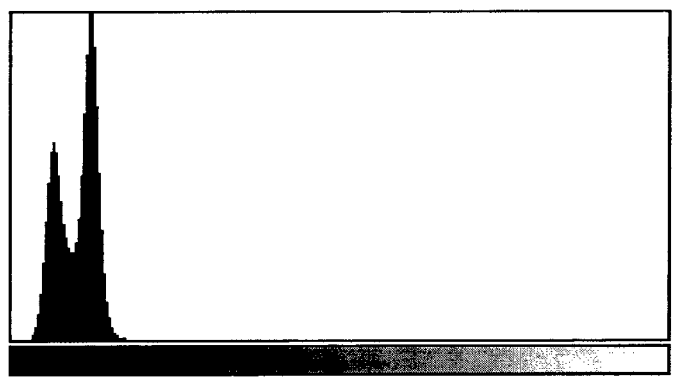

A histogram of grayness distribution inside the area of interest of the reference cross-section is obtained using special program (for, example, ImageJ—http://rsbweb.nih.gov/ij/), see FIG. 1.

The number of the components is defined as the number of peaks on the histogram of grayness distribution inside the area of interest on the reference cross-section. The histogram $I_i^1(z)$ of grayness distribution for each component inside reference cross-section (k=1) is approximated by normal distribution (Gaussian function):

$$I_i^1(z) = A_i^1 \exp\left[-\left(\frac{z - B_i^1}{C_i^1}\right)^2\right]$$

wherein i is index of a component; I is "intensity" (total number of pixels) of grayness z; $A_i^1$, $B_i^1$, $C_i^1$ are adjustable parameters; upper index "1" corresponds to number of cross-section (k=1).

Figure 2:
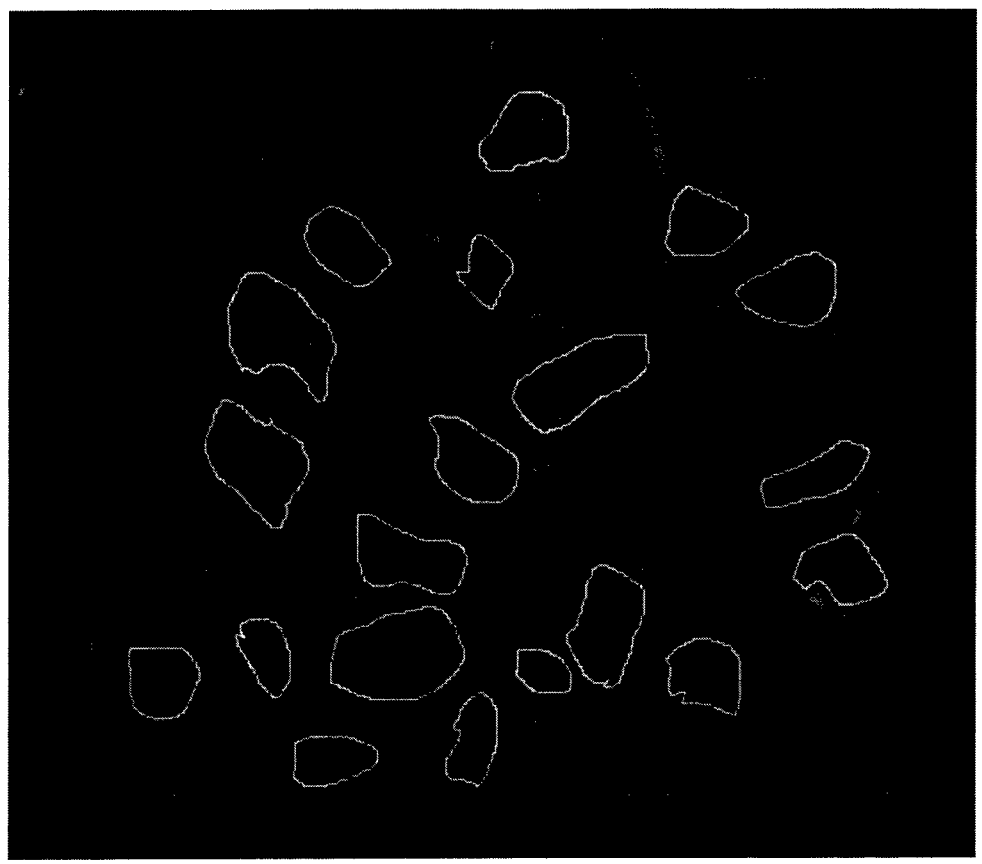
FIG. 2 shows an example of selecting the sub-areas, containing only one individual material, inside the total area of interest and obtaining the histogram of grayness distribution.
Figure 2:
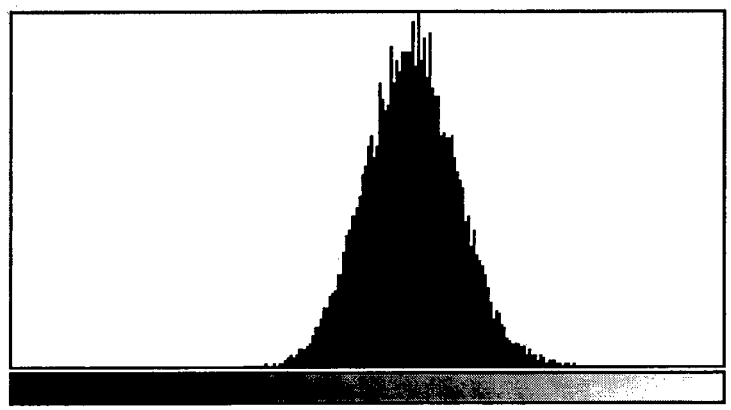

Example of hystogram of selected individual material is given in FIG. 2.

Figure 3:
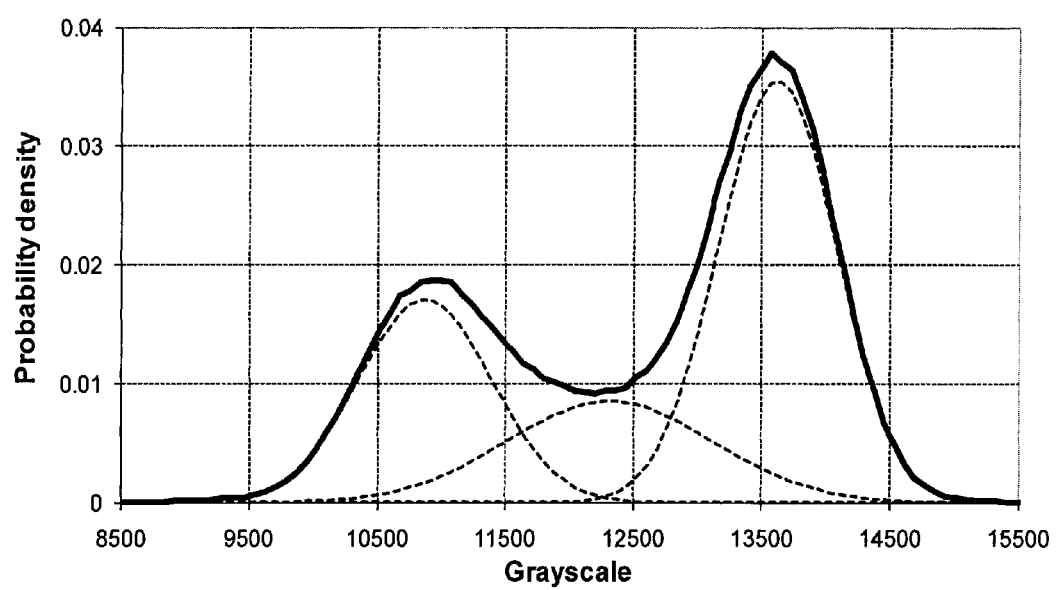
FIG. 3 shows an approximation of histogram using Gaussians as probability density functions.

Adjustable parameters for all components are crudely estimated from the histogram of grayness distribution inside the area of interest. Accurate estimation of adjustable parameters for the components is made by minimization of module of difference between the histogram of grayness distribution inside the area of interest of the reference cross-section and sum of normal distributions, corresponding to individual components $$\sum_{j=1}^{M}\left[H^1(z_j) - \sum_{i=1}^{N} A_i^1 \exp\left(-\left(\frac{z_j - B_i^1}{C_i^1}\right)^2\right)\right] \to 0 \quad (1)$$

wherein j is index of grayscale; M is total number of grayscales; N is total number of different components. Approximation result is shown on FIG. 3.

The fraction $a_i^1$ of the individual components inside the reference cross-section of the computer tomographic image is calculated as:

$$a_i^1 = \int A_i^1 \exp\left[-\left(\frac{z - B_i^1}{C_i^1}\right)^2\right] dz \quad (2)$$

Obtained parameters of Gaussians $A_i^1$, $B_i^1$, $C_i^1$ of the reference cross-section are used as initial parameters for minimization of module of difference between the real histogram of grayness distribution and it's approximation by sum of normal distributions (1) for next cross-section of the computer tomographic image (k=2) and so an.

To reconstruct the distribution and concentration of the contrast components along the sample the mininization of module of difference between the real histogram of grayness distribution and it's approximation by sum of normal distributions (1) and the expression (2) are applied to all cross-sections inside the area of interest of the computer tomographic image (k=1...K).

Figure 4:
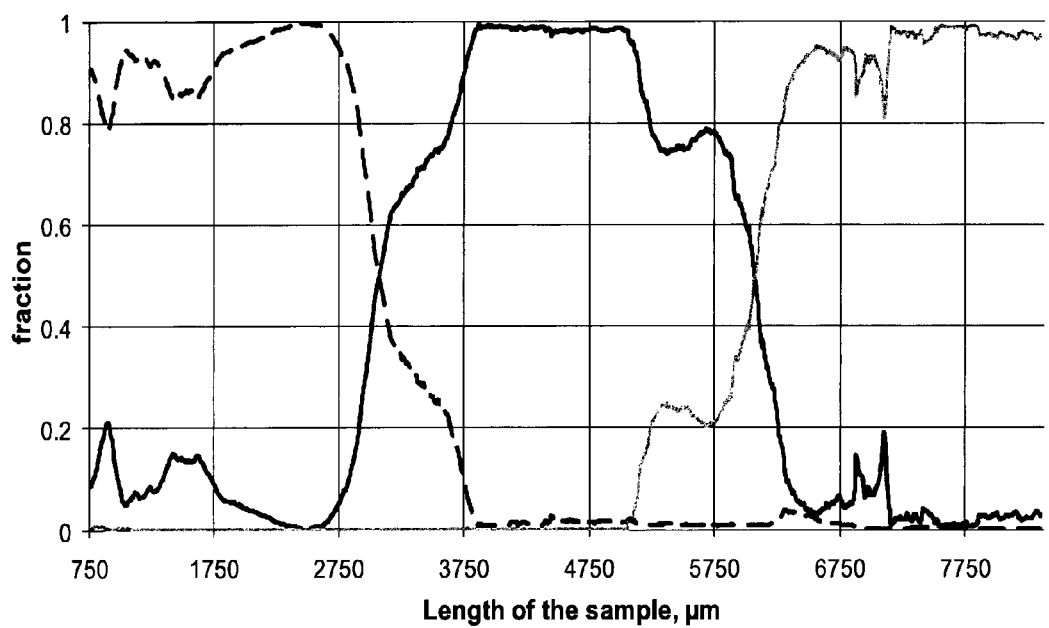
FIG. 4 shows an example of profile for mixture of three different materials.

Typical example of reconstructed profile for mixture of three different components is shown on FIG. 4.

According to the second embodiment of the invention a porous sample (artificial sample, consisting of sand grains and liquid glass as cement material) is scanned with X-ray and a computer tomographic image of the sample is obtained.

Then an area of interest inside of this computer tomographic image is selected and a first cross-section of the computer tomographic image (let us call it as reference cross-section and assign a number k=1) is defined. A histogram of grayness distribution inside the area of interest of the reference cross-section is obtained using special program (for, example, ImageJ—http://rsbweb.nih.gov/ij/), see FIG. 1.

Then, the sub-areas each containing only one individual component are selected inside the area of interest on the reference cross-section and histograms of grayness distribution of the individual components are obtained, see FIG. 2. All histograms are normalized by their area, i.e. by number of pixels. This way amount of pixels in every range of histogram must be divided by amount of all selected pixels. The histograms of all individual components are transformed to general scale, for example, to scale of histogram of total area of interest. Histogram of the area of interest of the reference cross-section is approximated by sum of histograms of individual components with some weight coefficients, corresponding to the areas that individual components occupy on this cross-section of the computer tomographic image.

Weight coefficients are obtained by minimization of module of difference between the real histogram of the area of interest of reference cross-section (k=1) and sum of histograms of individual components:

$$\left[\sum_{j=1}^{M}(|A_j^1 - b^1 B_j^1 c^1 C_j^1 - ...|)\right] \to 0 \quad (3)$$

wherein $A_j^1$, $B_j^1$, $C_j^1$, ... are vectors of values of histograms, $b^1$, $c^1$ etc are weight coefficients; j is index of grayscale; M is total number of grayscales; upper index "1" corresponds to number of cross-section (k=1).

Weight coefficients $b^1$, $c^1$ etc correspond to areas that individual components occupied on the reference cross-section of the X-ray image.

To reconstruct distribution and concentration of the contrast components along the sample, the procedure described above and including the mininization (3), is applied to all cross-sections inside area of interest of the computer tomographic image (k=1...K).

In the case of bad convergence of this problem, it is possible to extend the sub-areas containing individual components or check that all principle materials are taken into account.

The invention claimed is:
1. A method for determination of spatial distribution and concentration of contrast components in a heterogeneous sample comprising:
scanning the sample with an X-ray,
obtaining a computer tomographic image of the sample,
selecting an area of interest inside the obtained computer tomographic image of the sample,
processing the obtained computer tomographic image by a computer, the processing comprising:
defining a reference cross-section of the obtained computer tomographic image,
obtaining histograms of grayness distribution inside the area of interest in all cross-sections of the computer tomographic image,
determining spatial distribution and concentration of contrast components inside the area of interest along the sample by analyzing the histograms of grayness distribution inside the area of interest in the cross-sections of the computer tomographic image starting with the histogram of grayness distribution inside the area of interest in the reference cross-section.

2. A method of claim 1 wherein a step of analyzing the histograms of grayness distribution in the cross-sections of the computer tomographic image comprises:
defining a number of the contrast components as a number of peaks on the histogram of grayness distribution inside the area of interest in the reference cross-section,
approximating the histogram $I_i^1(z)$ of grayness distribution for each component inside the reference cross-section by normal distribution (Gaussian function):

$$I_i^1(z) = A_i^1 \exp\left[-\left(\frac{z - B_i^1}{C_i^1}\right)^2\right]$$

wherein
i is an index of a component;
I is "intensity" (total number of pixels) of grayness z;
$A_i^1$, $B_i^1$, $C_i^1$ are adjustable parameters corresponding to the reference cross-section;
upper index "1" corresponds to the reference cross-section,
approximately estimating adjustable parameters for all components from the histogram of grayness distribution inside the area of interest in the reference cross-section,
accurately estimating the adjustable parameters for the components by minimization of a module of difference between the histogram of grayness distribution inside the area of interest in the reference cross-section and a sum of normal distributions corresponding to the components $$\sum_{j=1}^{M}\left[H^1(z_j) - \sum_{i=1}^{N} A_i^1 \exp\left(-\left(\frac{z_j - B_i^1}{C_i^1}\right)^2\right)\right] \to 0$$

wherein
j is index of grayscale;
M is a total number of grayscales;
N is a total number of different components,
using obtained parameters of Gaussians $A_i^1$, $B_i^1$, $C_i^1$ as initial parameters for minimization of the module of difference between the histogram of grayness distribution and approximation of the histogram of grayness distribution by the sum of normal distributions for a next cross-section of the computer tomographic image,
sequentially applying the minimization of the module of difference between a histogram of grayness distribution and approximation of the histogram of grayness distribution by a sum of normal distributions corresponding to the components to all cross-sections inside the area of interest of the computer tomographic image using parameters of Gaussians $A_i^1$, $B_i^1$, $C_i^1$ obtained on previous cross-section as initial parameters for minimization for next cross-section, defining a fraction of the individual components inside each cross-section k by integration of individual Gaussians:

$$a_i^k = \int A_i^k \exp\left[-\left(\frac{z-B_i^k}{C_i^k}\right)^2\right] dz,$$

wherein k =1...K is a number of cross-section.

3. The method of claim 1 wherein a step of analyzing the histograms of grayness distribution in the cross-sections of the computer tomographic image comprises:
   selecting sub-areas inside the area of interest in the reference cross-section, each sub-area containing an individual component,
   obtaining histograms of grayness distribution of the individual components,
   normalizing all histograms by their area,
   transforming the histograms of grayness distribution of all individual components to a general scale,
   approximating the histogram of grayness distribution inside the area of interest in each cross-section by a sum of the obtained and normalized histograms of grayness distribution of the individual components with weight coefficients, corresponding to the selected sub-areas,
   defining the weight coefficients by minimization of the module of difference between the histogram of grayness distribution inside the area of interest in each cross-section and a sum of the histograms of the individual components:

$$\left[\sum_{j=1}^{M} (|A_j^1 - b^1 B_j^1 c^1 C_j^1 - \ldots|)\right] \to 0$$

wherein
$A_j^{\,1}$, $B_j^{\,1}$, $C_j^{\,1}$, are vectors of values of histograms,
$b^1$, $c^1$, ... are the weight coefficients;
j is index of grayscale; and
M is a total number of grayscales.

4. The method of claim 3 wherein the sub-areas containing the individual components are expanded.

* * * * *